United States Patent [19]

Powell

[11] Patent Number: 4,701,553
[45] Date of Patent: Oct. 20, 1987

[54] CYCLIZED UNSATURATED KETO ACIDS

[75] Inventor: Justin C. Powell, Fairfax, Va.

[73] Assignee: Texaco Inc., White, White Plains, N.Y.

[21] Appl. No.: 461,728

[22] Filed: Jan. 28, 1983

[51] Int. Cl.$^4$ .................... C07C 59/82; C10M 1/28; C10M 1/36
[52] U.S. Cl. .................... 562/504; 252/51.5 A; 562/503; 562/508; 564/189; 564/461; 564/462
[58] Field of Search .................... 562/504, 503, 508

[56] References Cited

U.S. PATENT DOCUMENTS 4,385,904  5/1983  Sawicki et al. .................... 44/56

FOREIGN PATENT DOCUMENTS 1018185  9/1977  Canada.

OTHER PUBLICATIONS

Chemical Abstracts, vol. 52, Abstract #1076b, 1958; Herz.
Chemical Abstracts, vol. 63, Abstract #13067b, 1965; Chiusoli et al.
Chemical Abstracts, vol. 88, p. 356, Abstract #62056y, 1978; Jankowski et al.

Primary Examiner—Donald B. Moyer
Assistant Examiner—Patricia M. Scott
Attorney, Agent, or Firm—Robert A. Kulason; Carl G. Seutter

[57] ABSTRACT

Unsaturated cyclic keto acid may be prepared by cyclizing alken-2-yl dicarboxylic acid anhydride with Lewis acid catalyst in anhydrous Friedel-Craft solvent. Amides of these unsaturated cyclic keto acids useful as friction improvers in lubricating oils, may be prepared by reaction of an amine such as ethanolamine with an unsaturated cyclic keto acid.

2 Claims, No Drawings

CYCLIZED UNSATURATED KETO ACIDS

FIELD OF THE INVENTION

This invention relates to novel cyclic keto acids which as their amides may find use as friction modifiers in lubricating oil compositions.

RELATED APPLICATION

The instant invention of Justin C. Powell, directed to cyclized unsaturated keto acids and their method of preparation, is related to the invention of Justin C. Powell and Stephen A. Levine, Ser. No. 461,730 filed, Jan. 28, 1983 directed to amides of said cyclized unsaturated keto acids, their method of preparation, and their use in lubricating oils.

BACKGROUND OF THE INVENTION

As is well known to those skilled in the art, it is desired to provide lubricating oil systems which minimize the friction between moving parts of a machine. Constant attempts are being made to find new techniques and compositions which may permit improved operation.

It is an object of this invention to provide novel compositions and a process for preparing these compositions. Other objects will be apparent to those skilled in the art.

STATEMENT OF THE INVENTION

In accordance with certain of its aspects, this invention is directed to a cyclized unsaturated keto acid prepared by the cyclizing of an alken-2-yl dicarboxylic acid anhydride with Lewis acid catalyst in an anhydrous Friedel-Craft solvent, wherein said alkenyl group contains at least four carbon atoms thereby forming reaction product; and recovering said reaction product.

DESCRIPTION OF THE INVENTION

The charge unsaturated cyclic keto-acids which may be employed in practice of the process of this invention may be those obtained by the rearrangement of $C_4$–$C_{28}$ (preferably $C_{10}$–$C_{25}$) alken-2-yl dicarboxylic acid anhydrides of the formula

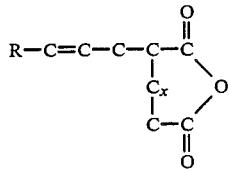

wherein R is a $C_1$–$C_{25}$ alkyl hydrocarbon group and x is an integer 0, 1, or 2.

Typical of these alken-2-yl dicarboxylic acid anhydrides are (i) n-tetradecen-2-yl succinic acid anhydride; (ii) n-penten-2-yl succinic acid anhydride; (iii) octadecen-2-yl succinic acid anhydride; etc.

These charge unsaturated cyclic keto acids may be prepared by contacting the alken-2-yl dicarboxylic acid anydride in Friedel-Craft solvent with a Lewis Acid catalyst in an anhydrous reaction system.

The Friedel-Craft solvents which may be employed include non-aqueous media which have heretofore been employed in Friedel-Craft reactions. These inert diluents typically include ethers including diethyl ether, ethylene glycol dimethyl ether, diethylene glycol dimethyl ether, etc; liquid halogenated hydrocarbons typified by methyl chloride, methylene dichloride, chloroform, carbon tetrachloride, trichloroethane, etc; liquid nitrohydrocarbons typified by nitrobenzene, nitropropane, nitrobutane; carbon disulfide, etc. The preferred solvent is methylene dichloride.

Preferably the Friedel-Craft solvent is present in amount of 50–1000 parts, say 100 parts per 100 parts of anhydride.

The Lewis Acid Catalyst which may be employed may include phosphorus pentoxide, toluene sulfonic acid, boron trifluoride, inorganic acids typified by sulfuric acid or hydrochloric acid; metal halides typified by aluminum chloride, aluminum bromide, zinc chloride, ferric chloride, ferrous chloride, zirconium chloride, antimony pentachloride, stannic chloride, beryllium chloride, etc. The preferred catalyst may be aluminum chloride.

Catalyst may be present in amount of 50–500 parts, say 160 parts per 100 parts of anhydride. This catalytic amount of Lewis Acid catalyst is found to permit reaction to be readily carried out.

Reaction may be carried out by contacting the anhydride in liquid Friedel-Craft solvent in the presence of the catalytic amount of Lewis Acid Catalyst. Typically temperature is 0° C.–20° C., preferably 10° C.–20° C., say 10° C. at atmospheric pressure.

Reaction normally may proceed with agitation over 12–24 hours, say 18 hours.

Work-up of the reaction mixuture may include acidification as by addition of 800–2400 parts, say 1040 parts of dilute hydrochloric acid plus ice. Solvent (typically 800 parts ethyl ether) is added. The ether layer is then separated and the solvent is evaporated. The product, if crystalline, may be recrystallized from the same or different solvent.

The product keto acid mixture, when prepared from succinic acid anhydride starting materials wherein x is 0, may include compounds containing 5 and 6 member rings typified by the following:

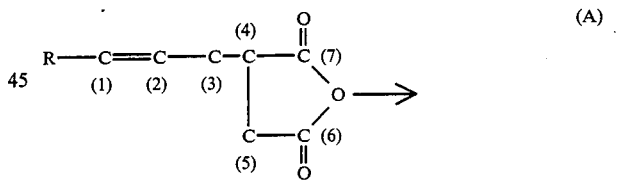

(A)

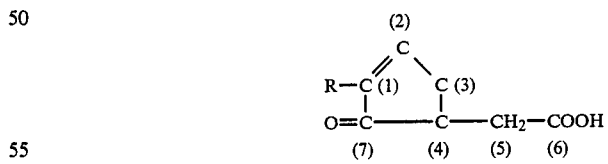

(B)

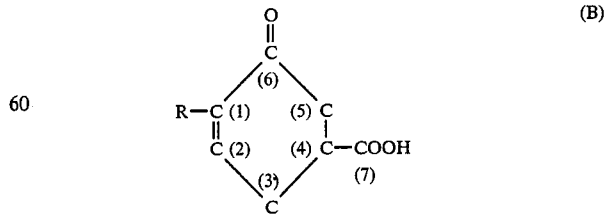

For convenience, the reaction product may be designated by reference to either five-membered rings (A) or six-membered rings (B). It will be understood by those skilled in the art both are formed during the reaction; and they are not separated in practice.

The cyclic acid products of this invention may be used (in the form of their lithium soaps) as components of greases.

When the product keto acid mixture is prepared from charge materials wherein x is 1 or 2 the products may include the following:

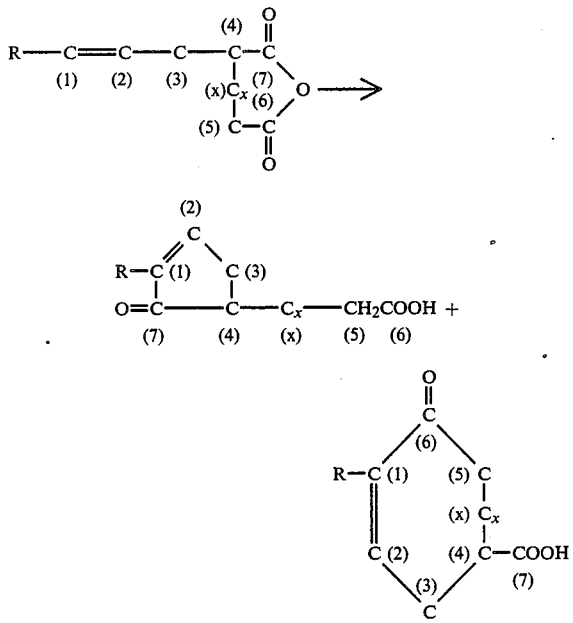

Although it may be possible to effect separation of the several product cyclic keto acids as by crystallization or by chromatographic methods (gas or liquid column chromatography), it is found that for many uses this is not necessary. If the product is to be further treated in accordance with this invention, satisfactory results may be attained with no further work-up or pretreating after preferred removal of the solvent.

Illustrative of the specific keto acids which may readily be prepared by the process of this invention may include those wherein x is zero and R is methyl or butyl or undecyl; those wherein x is one and R is methyl or butyl; and those wherein x is two and R is methyl, butyl, hexyl, etc.

The cyclized keto acid, typically prepared as noted and without separation of the several cyclic products from each other, may be amidated by reaction with an amine which contains, in addition to a first primary amino group, at least one other group which is an amine group or a hydroxyl group.

The most preferred amine reactants may be selected from the classes bearing the following designations:
   beta-hydroxyethylpolyethylenepolyamines
   polyethylene amines
   aminopolyols
     ethanolamines
     propanolamines
   methylol-methylamines
   imidazolines
   oxazolines When the amine reactant is from the class designated as beta-hydroxyethylpolyethylenepolyamines, it may have the formula, wherein a is an integer 1–10, preferably 2–10:

$HO(C_2H_4NH)_aH$

Illustrative of such compositions may be:
$HOC_2H_4NHC_2H_4NH_2$
$HOC_2H_4NHC_2H_4NHC_2H_4NH_2$
$HO(C_2H_4NH)_xH (x=1-10)$ When the amine reactant is from the class designated as polyethylenpolyamines; it may have the formula wherein b is an integer 1–10, preferably 2–10:

$H_2N(C_2H_4NH)_bH$

Illustrative of such compositions may be:
$H_2NC_2H_4NHC_2H_4NH_2$
$H_2NC_2H_4NHC_2H_4NHC_2H_4NH_2$
$H_2N(C_2H_4NH)_xH (x=1-10)$ When the amine reactant is from the class designated as aminopolyols, it may have the formula, wherein Z is —OH or —NH$_2$ at least one Z being —NH$_2$, and c is 1–6, $ZCH_2-(CHZ)_c-CH_2Z$ Illustrative of such compositions may be:
$HOCH_2-CHNH_2-CH_2OH$
$HOCH_2-CHOH-CHNH_2$
$H_2NCH_2-CHOH-CH_2NH_2$
$H_2NCH_2-(CHOH)_4-CH_2NH_2$
$HOCH_2-(CHNH_2)_4CH_2OH$ Aminopolyols, sometimes referred to as alkanolamines, may alternatively have the formula $HO(CH_2)_aNH_y$ wherein x is 1–3, y is 0–2 and a is 2–3
typified by
$(HOCH_2CH_2)_2NH$
$HOCH_2CH_2CH_2NH_2$
$(HOCH_2CH_2CH_2)_2NH$ Aminopolyols, which may also be referred to as amino polyglycols, may also have the formula
$H_2N(CH_2CH_2O)_yH$ wherein y=1–10
typified by
$H_2NCH_2CH_2OCH_2CH_2OH$
$H_2NCH_2CH_2OCH_2CH_2OCH_2CH_2OH$ When the amine reactant is from the class designated as methylol-methylamines, the formula, wherein e is an integer 0–2, may be:

$H_2N-CH_e(CH_2OH)_{3-e}$

Illustrative of such compositions may be:
$H_2N-C(CH_2OH)_3$
$H_2N-CH(CH_2OH)_2$
$H_2N-CH_2(CHOH)$ When the amine reactant is an ethanolamine or propanolamine, it may have the formula, wherein d is an integer 1–3, $(HOC_2H_4)_dNH_{3-d}$ or $(HOC_3H_6)_dNH_{3-d}$ Illustrative of such compositions may be:
$HOC_2H_4NH_2$
$(HOC_2H_4)_2NH$
$(HOC_2H_4)_3N$
$(HOC_3H_6)NH_2$
$(HOC_3H_6)_2NH$
$(HOC_3H_6)_3N$ When the amine reactant is from the class designated as imidazolines, it may include the compound having the formula (and it derivatives):

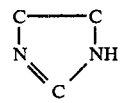

Illustrative of such compositions may be:

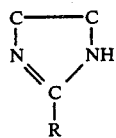

wherein R may be alkyl (such as methyl, ethyl, etc), alkenyl (typically heptadecen-8-yl), etc.

The preferred amine reactants may be:
ethanolamines
propanolamines
polyethylenepolyamines The charge cyclic unsaturated keto-acid is reacted with the amine, preferably in the presence of inert-diluent liquid. The preferred inert-diluents may be hydrocarbons which are liquid at the temperature of reaction. Hydrocarbons having a melting point below about 10° C. are suitable; and the preferred hydrocarbons may be paraffinic oils having a viscosity of 2–5000 centiStokes at 40° C., preferably 5–50 centistokes, say 18.5 centiStokes.

A preferred inert diluent may be a paraffinic distillate oil having a viscosity at 40° C. of 18.5 centiStokes.

The mole ratio of charge amine to charge cyclic acid may be 0.2–5, preferably 0.5–2 say 1.05:1 i.e. 5% greater than the amount dictated by the stoichiometry of the reaction. When using a diamine, these ratios may optionally be halved; etc.

Reaction of the acid and the amine may be carried out in liquid phase at the following conditions:

TABLE

| Condition | Broad | Preferred | Typical |
|---|---|---|---|
| Temperature °C. | 50–250 | 100–150 | 110–128 |
| Pressure, psig | 0–100 | 0–50 | 0 |
| Mole ratio of —NH$_2$ to —COOH | 0.2–5:1 | 0.5–2:1 | 1.05:1 |
| Wt Ratio of Diluent to Reactants | 0.2–5:1 | 0.5–2:1 | 1:1 |
| Time hours | 0.2–20 | 1–5 | 2 |

Reaction is preferably carried out in an inert atmosphere most preferably under nitrogen. As the reaction proceeds, one or more exotherms may be observed; and temperature control is commonly required. The reaction mixture typically becomes dark in color (reddish-brown).

During the course of the reaction, the following illustrative reaction is believed to occur (in the case of the six-member ring):

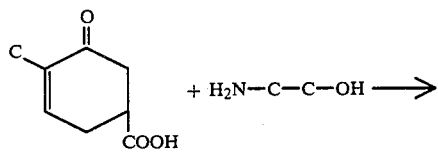

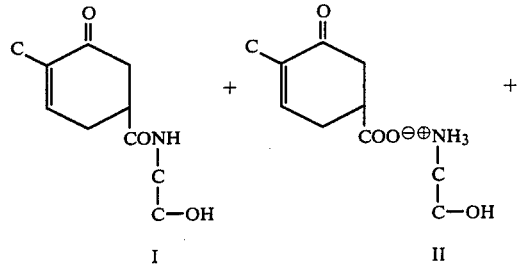

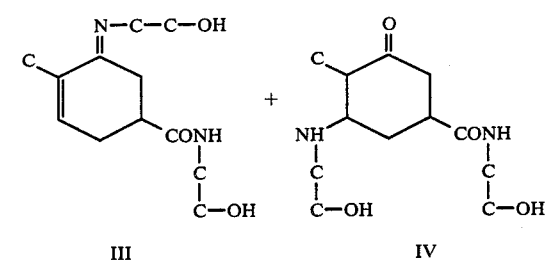

where henceforth structures II–IV shall be understood to be present also whenever structure I is mentioned; and although only the six-membered ring structure is shown, the five-membered ring compounds are also present. Despite the fact that not all of these compounds are simple amides, and indeed two of these structures are not amides at all (II for five- and six-membered rings), for the sake of simplicity we shall hereafter refer to them all (including stereochemical isomers) by the name amide.

It is possible to work up the reaction mixture to recover purified product by employing a low boiling hydrocarbon, e.g. xylene, as diluent and stripping this off at reduced pressure at the end of the reaction.

It is however a feature of the process of this invention that it is not necessary to work up the product. It may be used, as is, as an additive to a lubricating oil.

The products may include hydrocarbon-substituted cyclic unsaturated keto acid amides, including those which may be designated by the formula:

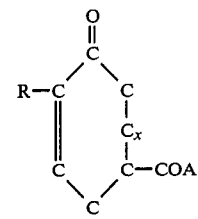

wherein R is an alkyl, cycloalkyl, aryl, alkaryl, aralkyl, alkenyl, or alkynyl group having at least two carbon atoms, x is an integer 0, 1, or 2, and A is an amine-containing moiety bonded to the —CO— group through a nitrogen atom.

Illustrative amide products which may be prepared may include those prepared from the following reactants:

TABLE

| Amine Reactant | Keto Acid Reactant |
|---|---|
| A. HOC$_2$H$_4$NH$_2$ (1 mole) | The cyclized keto acid derived from n-tetradecenyl succinic acid anhydride (1 mole) |

TABLE-continued

| Amine Reactant | Keto Acid Reactant |
|---|---|
| B. HOC$_2$H$_4$NHC$_2$H$_4$NH$_2$ (1 mole) | The cyclized keto-acid derived from n-tetradecenyl succinic acid anhydride (1 mole) |
| C. H$_2$NC$_2$H$_4$NHC$_2$H$_4$NH$_2$ (1 mole) | The cyclized keto acid derived from n-tetradecenyl succinic acid anhydride (1 mole) |
| D. HOCH$_2$—CHNH$_2$—CH$_2$OH (1 mole) | The cyclized keto acid derived from n-tetradecenyl succinic acid anhydride (1 mole) |
| E. H$_2$N—C(CH$_2$OH)$_3$ (1 mole) | The cyclized keto acid derived from n-tetradecenyl succinic acid anhydride (1 mole) |
| F. (HOC$_2$H$_4$)$_2$NH (1 mole) | The cyclized keto acid derived from n-tetradecenyl succinic acid anhydride (1 mole) |
| G. HOC$_2$H$_4$NH$_2$ (1 mole) | The cyclized keto acid derived from n-pentenyl succinic acid anhydride (1 mole) |
| H. H$_2$NCH$_2$—CHOH—CH$_2$NH$_2$ | The cyclized keto acid derived from n-pentenyl succinic acid anhydride (1 mole) |

In accordance with certain of its aspects, the novel amide products may be used as friction modifiers in lubricating oils, as rust inhibitors in lubricating oils or in motor fuels, etc.

When the products are used in lubricating oil compositions, they may be present in minor friction modifying amount of 0.01–50 parts, preferably 0.5–5 parts, say 1 part per 100 parts of lubricating oil composition.

The lubricating oil compositions which may be formulated may contain various lubricating fluids (hereinafter referred to as oils) which may typically have viscosities of about 2–5000 centiStokes at 40° C. or 0.01–2000 centiStokes at 100° C. Among natural hydrocarbonaceous or hydrocarbon oils are paraffin-base, naphthenic-base, asphaltic-base and mixed base oils.

Illustrative of synthetic oils are: hydrocarbon oils such as polymers of various olefins having 2–12 carbon atoms; alkylated aromatic hydrocarbons; and non-hydrocarbon oils, such as polyalkene oxides, aromatic ethers, carboxylate esters, phosphate esters, and siliconecontaining compounds. The preferred media are the hydrocarbonaceous media, both natural and synthetic.

These oils may be used individually or together whenever miscible or made so by the use of mutual solvents.

In order to permit facile handling of the compositions they may be employed or handled in concentrates which contain 0.1–200 parts, say 20–50, typically 50 parts of composition in 100 parts of diluent. Diluent may be one which is compatible with or identical to, the principal component with which the additive is to be formulated. When the composition is to be used as an addition to a hydrocarbon-containing lubricating oil for example, the concentrate may contain eg 50 parts of additive per 100 parts of a lubricating oil-miscible composition such as lubricating oil se.

The formulated oils containing the additive may normally contain dispersants, detergents, wear inhibitors, anti-oxidants, anti-foamants, and other such additives as might normally be found in crankcase oils, automatic transmission fluids, power steering fluids, gear oils, brake fluids, greases etc.

DESCRIPTION OF THE PREFERRED EMBODIMENT

Practice of the process will be apparent to those skilled in the art from the following wherein, as elsewhere in this description, all parts are parts by weight unless otherwise set forth. In the formulae, as elsewhere, all unfilled valence bonds may be filled with hydrogen atoms or inert substituents.

EXAMPLE 1

This example represents the best mode of carrying out the process of this invention.

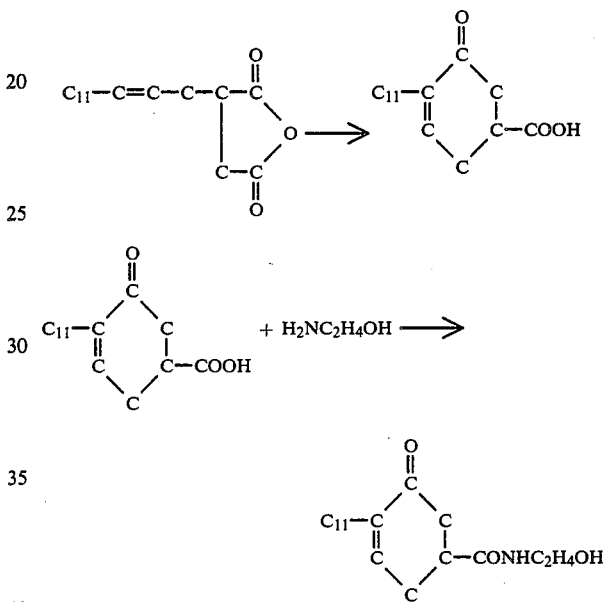

KETONIZATION OF TDSAA

A solution of 294.44 g (1.00 moles) of n-tetradecen-2-yl succinic anhydride (TDSAA) (Humphrey Chemical, distilled grade) is made in 300 ml of dichloromethane (Aldrich) by heating and stirring to about 50° C. in a 1-L Morton-type resin kettle with 4-necked head equipped with mechanical stirrer, nitrogen inlet, Claisson adapter with thermometer and CaCl$_2$ drying-tube outlet, and a 250-ml Erlenmeyer flask containing 160.0 g (1.2 mole) of aluminum chloride (Aldrich) connected by Gooch tubing. A slow stream of N$_2$ is passed through the apparatus at all times.

After cooling the solution to about 10° C. with an NaCl-ice bath, the aluminum chloride is added slowly over 1.0 hour with stirring to keep the reactants well mixed, and the temperature is moderated between 10° and 20° C. After the addition is complete, the mixture is allowed to stand overnight without stirring. The reaction mixture solidifies to a crystalline-looking pea-green colored mass.

The reaction mixture is then worked up by transfer to a 4-liter beaker containing a cold mixture of 800 ml of distilled water, 240 g concentrated (ca 38%) hydrochloric acid, and about 200 g of ice. Then 800 ml of ethyl ether is added and the mixture is stirred. The two-phase system is transferred to a 6-liter separatory funnel. The lower aqueous phase is separated and extracted three times with 150-ml portion of ethyl ether. The combined ether phases are dried over CaCl$_2$ overnight then filtered through diatomaceous earth and evaporated (rotary evaporator to 130° C., 5 mm Hg) to yield 283.27 g (86.7% of theory for keto acids) of crude keto-acid mixture of compounds consisting principally of 5- and 6-membered rings and exocyclic unsaturated conjugated ketone acids, including 2-n-undecylcyclohexene-3-one-5-carboxylic acid. The first equation set forth supra represents the formation of one of the product cyclic keto acids-that containing the six-membered ring: it will be understood however that the reaction mixture may contain other products including the five-membered ring and (after reaction with the amine) its amide reaction products.

Analysis % C, 70.3; % H, 10.0 SP-455 Nap. Mod Acid Neut No., 213; $^{13}$CNMR confirms mixture of unsaturated cyclic ketone acids.

Preparation of the Reaction Product from the Amine and Keto Acid

A flask is charged with 58.8 grams (0.2 moles) of the crude keto-acid, 12.2 grams (0.2 moles) of monoethanolamine, and 71.0 grams of a paraffinic distillate oil of approximate viscosity at 40° C. of 18.5 cSt. The mixture is stirred and heated under an inert atmosphere for two hours at 110°–128° C. Several exotherms are noted during the reaction and cooling baths are applied to control the temperature. The product is a reddish-brown liquid having the following analysis % N (calc 2.1) found 2.0.

Results comparable to Example I may be attained if the amine is as follows:

TABLE

| Example | Amine |
| --- | --- |
| II | HOC$_2$H$_4$NHC$_2$H$_4$NH$_2$ |
| III | H$_2$NC$_2$H$_4$NHC$_2$H$_4$NH$_2$ |
| IV | HOCH$_2$—CHNH$_2$—CH$_2$OH |
| V | H$_2$N—C(CH$_2$OH)$_3$ |
| VI | (HOC$_2$H$_4$)$_2$NH |
| VII | H$_2$N—C$_2$H$_4$—NH$_2$ |

Examples II–VI use mole ratio of 1:1.

Results comparable to Example I may be attained if the acid (reacted with the amine) is the following:

TABLE

| Example | Acid |
| --- | --- |
| VIII | The cyclic keto acid derived from n-penten-2-yl succinic acid anhydride |
| IX | The cyclic keto acid derived from octadecen-2-yl succinic acid anhydride |

EXAMPLES X*–XI

In these Examples which show use of a typical amide product as a friction modifier in a lubricant, a reference standard hydrocarbon commercial lubricating oil composition (10W-40) is employed which contains zinc dithiophosphate wear inhibitor, ashless antioxidants, succinimide dispersant, calcium detergent, and a viscosity index improver.

In control Example X*, the reference standard lubricating oil is subjected to the small engine friction test in which a motored single cylinder engine is used to measure the frictional characteristics of the oil. The values of torque are those measured during the test; and the results of this test have been found to correlate with field experience using a large fleet of cars under varied on-the-road driving conditions. The percentage change in torque correlates with a percent change in fuel economy. The torque (in foot pounds) at various oil temperatures is determined.

In Experimental Example XI, one part of the reaction product of Example I is added to 99 parts of reference standard oil; and this sample is subjected to the small engine friction test. The results are as follows:

TABLE

| Example | Liquid | Torque (foot-pounds) |
| --- | --- | --- |
| X* | Reference Standard | 2.70 |
| XI | Reference Standard + 1% of Ex I Amide | 2.44 |

From the above table, it is apparent that use of the novel composition permits a desirable decrease in friction by a substantial value—a 9.6% decrease in the torque.

Comparable results may be attained if the compositions of Examples II–IX are employed.

Although this invention has been illustrated by reference to specific embodiments, it will be apparent to those skilled in the art that various changes and modifications may be made which clearly fall within the scope of this invention.

I claim:

1. A cyclized unsaturated keto acid prepared by the process which comprises cyclizing a C$_{10}$–C$_{25}$ alken-2-yl dicarboxylic acid anhydride with a Lewis acid catalyst in anhydrous Friedel-Craft solvent thereby forming product cyclized unsaturated keto acid; and recovering product cyclized unsaturated keto acid.

2. A cyclized unsaturated keto acid prepared by the process which comprises cyclizing n-tetradecen-2-yl succinic acid anhydride with aluminum chloride in anhydrous Friedel-Craft solvent thereby forming product cyclized unsaturated keto acid; and recovering said product unsaturated cyclized keto acid.

* * * * *